United States Patent [19]  [11] Patent Number: 4,803,288
Kitamura et al.  [45] Date of Patent: Feb. 7, 1989

[54] PROCESS FOR PRODUCING MACROCYCLIC ESTER COMPOUNDS

[75] Inventors: Satoshi Kitamura; Takashi Tobita, both of Chiba; Motoki Kanazawa, Tokyo; Masahiro Shiozaki, Kanagawa, all of Japan

[73] Assignee: Nisso Petrochemical Industries Co., Ltd., Tokyo, Japan

[21] Appl. No.: 136,437

[22] Filed: Dec. 17, 1987

Related U.S. Application Data

[63] Continuation of Ser. No. 841,893, Mar. 20, 1986, abandoned, which is a continuation-in-part of Ser. No. 567,158, Jan. 4, 1984, abandoned, which is a continuation of Ser. No. 395,505, Jul. 6, 1982, abandoned.

[51] Int. Cl.$^4$ ............................................. C07D 321/00
[52] U.S. Cl. ..................................................... 549/267
[58] Field of Search ......................................... 549/267

[56] References Cited

U.S. PATENT DOCUMENTS 4,165,321  8/1979  Harris et al. .......................... 549/267
4,251,448  2/1981  Bauer et al. .......................... 549/267

OTHER PUBLICATIONS

English Translation of Japan Patent Publication No. 120581-1980, 09/17/80.

Primary Examiner—Richard L. Raymond
Attorney, Agent, or Firm—George B. Oujevolk

[57] ABSTRACT

An improved process for producing a macrocyclic ester compound comprises decomposing and cyclizing linear ester compounds, from high to low condensate, to the macrocyclic ester, with the addition of glycol or oligoester compound of which the component is similar as those of said linear ester compounds. By this addition the reaction proceeds easily for a long time, and its efficiency is improved.

1 Claim, No Drawings

PROCESS FOR PRODUCING MACROCYCLIC ESTER COMPOUNDS

This application is a continuation of application Ser. No. 841,893, filed Mar. 20, 1986, now abandoned, which is a continuation-in-part of application Ser. No. 567,158, filed Jan. 4, 1984, now abandoned, which is a continuation application of Ser. No. 395,505, filed July 6, 1982, now abandoned.

BACKGROUND OF THE INVENTION

The present invention relates to an improved process for producing macrocyclic ester compounds used for musk perfumes.

BRIEF DESCRIPTION OF THE PRIOR ART

Macrocyclic ester compounds such as ethylene brassylate have a musk-like fragrant odor and are useful for musk perfume. As is well known, these compounds have been obtained in such a manner that the corresponding aliphatic dicarboxylic acid or its alkyl ester is reacted with alkylene glycol, or otherwise, the aliphatic dicarboxylic acid is reacted directly with alkylene oxide, to linear polyester and then the polyester is thermally depolymerized to monomeric units which are cyclized simultaneously. Usually, the above cyclization reaction followed by thermal depolymerizaton has been carried out with heating under reduced pressure in the presence of a catalyst.

Further, according to various conventional techniques, mentioned above, this cyclization reaction is accompanied by further polycondensation of the linear polyester and intermolecular crosslinking reaction in the reaction system. Consequently, the viscosity of the reaction mixture is so raised that its agitation is very difficult and its thermal conductivity is considerably reduced. As a result, the yield is decreased and a quality change of the macrocyclic ester compound occurs. Moreover, decomposed gas is generated so that the odor and color of the macrocyclic ester compound distilled from the reaction system are degraded. Those various defects are typical of these conventional methods.

As one method for improving the many defects mentioned above, the addition of an inert medium having a high boiling point to the reaction system to decrease the apparent viscosity has been disclosed in Japanese unexamined application No. 81875/1980, Japanese unexamined application No. 56681/1978, and Japanese unexamined application No. 51472/1981.

In practice, the medium employable for the foregoing process is liquid paraffine or solid paraffine. As is well known, this medium can not dissolve the linear polyester, and has only the effect of dispersing the highly viscous polyester into the medium having somewhat low viscosity. Consequently, in some cases, the polyester coagulates into large blocks and, because of the use of a large amount of the medium, the efficiency of its reactor is extremely reduced. Further, the distilled macrocyclic ester compound is dissolved in the medium, so its separation requires complicated operations.

As another example hereinbefore mentioned, a process for performing depolymerization and cyclization in the presence of polyoxyalkylene glycol and its derivative, monohydlic alcohol and its derivative or monovalent fatty acid and its derivative, either of which has a high boiling point, is described in Japanese unexamined application No. 120581/1980. According to the process, ether bonds of the added polyoxyalkylene glycol are decomposed and thereby various decomposed compounds are produced or decomposed gases are generated and consequently, a decrease in the degree of vacuum is brought about or the quality of the macrocyclic ester compound is degraded. Further, the odor of the monohydric alcohol, the monovalent acid or these derivatives are mixed in the distillate and have a detrimental influence on the odor of the macrocyclic ester compound from the view point of its use as perfume. These phenomena were cited as defects of these conventional processes.

In U.S. Pat. No. 4,165,321, Harris et al proposed the process in which a specified amount of monocarboxylate moieties is added to the reaction system and a specific agitating apparatus is employed. The monocarboxylate is added to the reaction system on purpose in order to prevent the excess polycondensation reaction. But, the above addition can not completely prevent the excess poly condensation, so the specific agitator should be employed in order to continue the agitation for a long time. In this process, the monocarboxylate is independent on the components of the macrocyclic ester compound, and, as a result, it tends to soil the product and further, degrade its odor.

In U.S. Pat. No. 4,251,448, Bauer et al proposed the process in which the polyester produced in advance is introduced dropwise to a distillation apparatus. The purpose of the dropwise addition is to avoid the agitation difficulty mentioned above. In other words, only a little amount of the polyester is always present in the distillation apparatus, and can decompose without the agitation. However, this process requires an additional vessel in which the polyester is kept in a molten state for a long time, and takes an extremely long time to the completion of the depolymerization. Further, a part of the added polyester, even if a little, stays in the distillation apparatus and it polyemerizes and crosslinks gradually. As a result, the total product yield becomes extremely low.

These unpreferable phenomena were cited as defects of these above processes.

Previously, the inventors proposed the process for producing the macrocyclic ester compound in Japanese application No. 7279/1981 in which a similar method to that of the present invention is carried out by using the linear aliphatic polyester and the same kind of oligoester having the specified degree of condensation.

Afterwards, the inventors have studied this process more closely and as a result, it was discovered that, even if a condensate having a low degree of condensation and being free from the peculiar physical properties in high polymers besides the conventional aliphatic polyester is used, the macrocyclic ester compound can be produced by means of adding the same kind of oligomer or the same kind of glycol to the reaction system and not adding any other compound related to the components of the macrocyclic ester compound. As the additive, monoester, diester or oligo-ester produced from the glycol and the dicarboxylic acid as components of the macrocyclic ester compound and/or a glycol as one component of the macrocyclic ester compound may be used without occurrence of the aforementioend disadvantages and thus, the inventors discovered that the macrocyclic ester compound can be produced easily and efficiently, and they accomplished the present invention.

SUMMARY OF THE INVENTION

The present invention relates to an improved process for producing a macrocyclic ester compound, composing adding glycol and/or an oligo-ester compound having the general formula (I):

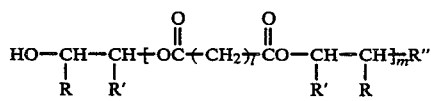

to a reaction system containing a linear ester compound having the general repeating unit formula (II):

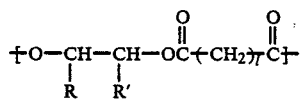

at an optional reaction stage so as to obtain a macrocyclic ester compound having the general formula (III):

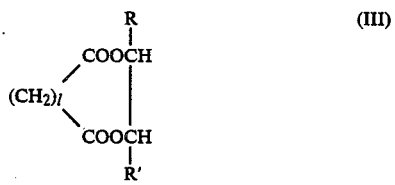

where R and R' both denote hydrogen atom or one denotes a hydrogen atom and the other denotes a methyl group or an ethyl group, l is a positive integer in the range of 6 to 14, m is a positive integer indicating an average condensation degree in the range of zero to 20 or less and R'' denotes a hydroxy group or a group having the formula:

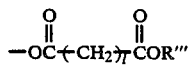

where R''' denotes a hydrogen atom or an alkyl group having 1 to 3 carbon atoms.

These macrocyclic ester compounds are used for musk perfume.

DETAILED DESCRIPTION

In the process of the present invention, the linear ester compound represented by the general formula (II), as the raw material of the macrocyclic ester compound, can be produced by using conventional processes producing polyester. For example, a raw material, i.e., dicarboxylic acid having the general formula, HOOC–(CH₂)ₗCOOH or its ester is reacted with glycol having the general formula,

as another raw material, if necessary, in the presence of a conventional catalyst, by means of an esterification reaction or ester exchange reaction, to produce bis-glycol ester of the dicarboxylic acid or its polycondensate having lower degree of condensation. Further, the bis-glycol or the polycondensate having low degree of condensate is heated to about 270° C., if necessary, in the presence of a conventional polycondensation catalyst. As the reaction proceeds, its reaction system is kept under reduced pressure, and finally 0.1 to 50 mmHg and, as its polycondensation proceeds, the ester compound can be produced.

As hereinbefore set forth, the linear ester compound comprises these condensates ranging from a lower molecular condensate which does not have viscosity or elasticity peculiar to higher molecular polycondensates, and to a high molecular polycondensate having the above-mentioned physical properties. The condensation degree of the lower molecular condensate is controlled by the combination of dicarboxylic acid and glycol used as raw materials. The lower molecular condensate obtained after the following stage of the reaction system is desirably used. The stage is equal to, so-called, the first step of a polyester polycondensation in which the reaction temperature is in the range of 230° C. to 260° C. and the reaction pressure is in the range of 30 to 50 mmHg.

As the dicarboxylic acid, one raw material of the linear ester compound in the present invention, suberic acid, azelaic acid, sebasic acid, nonamethylene-1,9-dicarboxylic acid, decamethylene-1, 10-dicarboxylic acid(dodecanedioic acid), undecamethylene-1,11-dicarboxylic acid(brassylic acid), and thapsic acid or the like may be used. As the ester of the acid, dimethyl ester and diethyl ester or the like may be used. Those acid components may be used as one kind or a mixture of two or more.

As the glycol, another compartment of the raw material, ethylene glycol, propylene glycol and 1,2-butylene glycol or the like may be used. The glycol components may be used as one kind or a mixture of two or more.

As hereinbefore set forth, in the conventional process for producing a macrocyclic ester compound represented by the general formula (III) from the linear ester compound, polycondensation of the linear ester compound is accelerated and after it reaches a high degree of polycondensation, an appropriate catalyst for depolymerization and cyclization is added to the reaction system. Both depolymerization and cyclization are carried out by heating under reduced pressure. Thus, the macrocyclic ester compound distilled outside the reaction system is collected and produced.

According to the conventional process, both depolymerization and cyclization reactions for producing the macrocyclic ester compound and the polycondensation reaction take place competitively and thereby the degree of condensation of the polyesterr left in the reactor is greatly increased. Further, in addition to the two above-mentioned reactions, crosslinking reaction of the linear polyester occurs and after a while agitation becomes difficult. Further, generation of the macocyclic ester compound virtually stops and instead generation of other decomposed gas occurs.

On the other hand, according to the process of the present invention, glycol and/or oligo-ester compounds represented by the general formula (I) are/is added to the reaction system at the depolymerization and cyclization stage and thereby the degree of condensation of the linear ester compound in the reaction system is not raised above the necessary degree, so the cross-linking phenomenon does not take place from the initial stage to the final reaction stage. As a result, the macrocyclic ester compound can be generated constantly.

As a glycol and/or oligo-ester being represented by the general formula (I), any reaction compound of the following glycol with the acid having a general formula, HOOC(CH$_2$)$_l$COOH may be used in addition to ethylene glycol, propylene glycol, and 1,2-butylene glycol, a raw material of the linear ester compound, where l is a positive integer from 6 to 14. For example, the oligomer having an average degree of condensation of 20 or less, and comprising a mono-glycol ester, bis-glycol ester or glycol carboxylate may be desirably used. Further, one kind of glycol or a mixture of two or more, or the reaction product of the glycol with one kind or two or more of dicarboxylic acids may be used.

In carrying out the process of the present invention, at first the linear ester compound is maintained in a molten stage, with agitation and under reduced pressure of 50 mmHg or less with or without a catalyst and thereby, the same glycol as one component of the linear ester compound is initially distilled out. Meanwhile, the glycol distillation virtually terminates. After the stage, when reaction pressure is decreased gradually to 0.1 to 1.0 mmHg, with the addition of the catalyst, if not added the prior reaction stage, then both the macrocylic ester compound and glycol are initially distilled out. Following the above distillation, the viscosity of the linear ester compound is greatly increased and agitation becomes difficult gradually, then the compound having the general formula (I) is preferably added continuously or intermittently to the reactor, for example, from its bottom, in proportion to the distillation rate and therby, the macrocyclic ester compound and glycol are simultaneously distilled out without causing a further increase in viscosity.

In the case of using the oligo-ester, the macrocyclic ester compound is continuously distilled out while the addition continues, but, if necessary, the reaction can be terminated at an optional stage.

In the process of the present invention, all kinds of conventional depolymerization and cyclization catalysts can be used for producing the macrocyclic ester compound from the linear ester compound represented by the general formula (II). For example, a lead compound including lead nitrate and lead borate, dialkyltin oxide, a complex catalyst containing an inorganic lead compound such as lead carbonate or lead sulfate with alkali metal, alkaliearth metal or aluminium alkoxide, aluminium alkoxide only, aluminium compounds having a carbonate radical, titanium alkoxide or the like may be used. The catalyst is used usually in the range of 0.1 to 10 percent by weight of the dicarboxylic acid used as the raw material. The entire amount of this catalyst may be added to the reaction system at the same time when the linear ester compound is charged, then at the addition of the glycol or oligo-ester, catalyst charge is not necessary. Alternatively, any part of this catalyst amount may be added to the linear ester compound charged to the reaction system, and the remaining part may be added to the glycol or oligo-ester. Thus, this catalyst may be added fully or partially at any time from the start of the linear ester compound reaction to the start of addition of the glycol or oligo-ester, or may be added to the linear ester compound or the glycol or oligo-ester, both prior to their addition to the reaction system. In all cases, this catalyst has the same effect on the depolymerization and cyclization reaction.

Macrocyclic ester compounds able to be produced by processes of the present invention and exemplified by the general formula (III) are shown with IUPAC nomenclature as follows;

2,5-dioxa-1,6-dioxocycloalkane, 3-methyl-2,5-dioxa-1,6-dioxocycloalkane, 3,4-dimethyl-2,5-dioxa-1,6-dioxocycloalkane, 3-ethyl-2,5-dioxa-1,6-dioxocycloalkane or 3,4-diethyl-2,5-dixa-1,6-dioxocycloalkane, in which the ring member is in the range from 10 to 20.

Of these compounds, the cycloalkanes having from 12 to 17 ring members are preferable, and more preferable compounds are;

2,5-dioxa-1,6-dioxocyclododecane(ethylene sebacate), 2,5-dioxa-1,6-dioxocyclohexadecane(ethylene dodecanedioate), 2,5-dioxa-1,6-dioxocycloheptandecane(ethylene brassylate), 2,5-dioxa-1,6-dioxocycloeicosane(ethylene thapsate), 3-methyl-2,5-dioxa-1,6-dioxocyclohexadecane(propylene dodecanedioate), 3-methyl-2,5-dioxa-1,6,dioxocycloheptadecane (propylene brassylate), and so on.

Through use of the process of the present invention, the utilization efficiency of the depolymerization and cyclization reactor can be remarkably enhanced and further, if necessary, the above reaction step may be terminated at its optional stage. In the case of exhausting the reaction residue, the compound exemplified by an alkylene glycol as hereinbefore set forth is additionally added and thereby the residue is very easily decomposed, dissolved in the glycol and can be exhausted. This glycol solution contains bis-glycol ester of the dicarboxylic acid same as the component of the linear ester compound having the general formula (II). Consequently, after filtering insoluble materials such as decomposed catalyst or others from this glycol solution, the bis-glycol in the solution can be utilized repeatedly as any part or all of the linear ester compound represented by the general formula (II). Even if a mechanism for the preferred effect in the process of the present invention is not completely understood, a disproportionation or depolycondensation reaction will occur by adding the glycol and/or the oligo-ester and, as a result, agitation can be achieved easily and thermal conductivity can be improved without further raising the degree of polycondensation compared with conventional processes. Simultaneously, the depolymerization and cyclization will not necessarily require the polyester to have a sufficient higher degree of condensation as considered previously. It is concluded that even a linear ester compound having a very low degree of condensation can be also used very easily for the depolymerization and cyclization in the process of the present invention.

Thus, the distilled reaction product is rectified, if necessary, and thereby, a macrocyclic ester compound having a high purity and desirable fragrant odor can be obtained.

The glycol which is distilled out in producing the linear ester compound, in producing the macrocyclic ester compound or in the rectifying step may be repeatedly used.

According to the present of the present invention, the macrocyclic ester compound can be produced from the linear ester compound always having practically optional viscosity with high yield and high efficiency.

For the purpose of giving those skilled in the art a better understanding of the invention, the following Exxmples and Comparison Examples are given. (all parts being "parts by weight")

Example 1

(The process for producing linear ester compound)

244 parts of brassylic acid and 124 parts of ethylene glycol was charged into a reactor fitted with a distilling tower and an agitator and those reactants were heated with agitation under the ambient pressure.

The reaction temperature was maintained in the range of 150 to 220° C. for three hours. After 35.7 parts of water had been distilled out, the reaction temperature was raised to 230° C. and the pressure was gradually decreased to 40 mmHg. The reaction was continued with heating and, when 48 parts of ethylene glycol totally distilled out, the reaction was teminated. The final temperature was 245° C.

The resulting product was a lower molecular weight condensate and it did not indicate tackiness in the molten state.

(The process for producing macrocyclic ester compound)

142 parts of the above linear ester compound and 0.2 parts of dibutyl tin oxide were charged into a reactor fitted with an agitator for highly decreased pressure reaction. The reaction system was heated and the pressure was gradually reduced.

At 240° C. and under 5 mmHg, both ethylene glycol and ethylene brassylate began to distil out notably. Those products, ethylene glycol and ethylene brassylate separated into two layers in the receiving vessel, so the lower layer, ethylene glycol was separated out and continuously added to the bottom of the reactor in proportion to the amount of ethylene glycol which was distilling out.

During the period of this reaction, the temperature was kept in the range of 260 to 270° C., and the agitator torque at 100 r.p.m. was almost constantly kept in the range of 1.5 to 2.0 kg-cm.

This reaction was continued for 8 hours whereby 129 parts of ethylene brassylate was produced and its yield relative to the used brassylic acid was 95.6%.

Comparison Example 1

In the above-mentioned process for producing the macrocyclic ester compound in Example 1, the addition of the distilled ethylene glycol was not entirely achieved and the similar reaction was continued and thereby, 10 parts of ethylene brassylate was distilled out during one hour. But the torque at 100 r.p.m. was gradually raised and finally reached 9 kg-cm and then its agitation was stopped.

Further, the reaction without agitation was continued for 7 more hours, but the reaction mixture was crosslinked and colored with its foaming and only 5 more parts of ethylene brassylate was distilled out. The total yield was only 11.1% relative to the used brassylic acid.

Example 2

(The process for producing oligomer for the addition use)

2,440 parts of brassylic acid and 1,340 parts of ethylene glycol were charged into a reactor fitted with a distilling tower and an agitator, and those reactants were heated in the range of 150 to 220° C. for two hours and its esterification was accelerated. After 355 parts of water had been distilled out, the temperature was raised up to 230° C. and excess ethylene glycol was distilled out, then oligomer was produced. The average molecular weight of the oligmer was assumed to be about 400 from the amount of the glycol distilled and its hydroxy value.

(The process for producing macrocyclic ester compound)

142 parts of the linear ester compound in Example 1 and 0.4 parts of lead nitrate were charged into a reactor fitted with an agitator and high vacuum means. The reaction system was gradually heated and kept under reduced pressure. At 240° C. and under 5 mmHg, distillation of both ethylene glycol and ethylene brassylate initiated, then the viscosity of the reaction system gradually increased.

In this stage, the oligomer mentioned above was entirely molten and was continuously added to the reactor from its bottom so as the amount of the reaction mixture was kept constant. During the period of this operation, the reaction temperature was kept in the range of 270 to 280° C. and its pressure in the range of 0.5 to 2.0 mmHg. Further, the viscosity of the reaction system was kept rather lower compared with that prior to the oligomer addition and thereby, both ethylene glycol and ethylene brassylate continuously distilled out.

The oligomer addition from initiation to termination required 25 hours and, after the termination of oligomer addition, the reaction was continued for two more hours at the same temperature and at the same pressure. Then the viscosity was raised such that the agitation might become difficult and at this stage, the reaction was finished.

The distilled amount of ethylene brassylate was 2,600 parts and its yield was 96.3% relative to the brassylic acid used.

Example 3

(The process for producing oligomer)

2,300 parts of dodecanedioic acid and 1,300 parts of ethylene glycol were charged into a reactor fitted with a distilling tower and an agitator and those reactants were heated in the range of 150 to 210° C. for two hours for the esterification reaction. When 356 parts of water had been distilled out, its internal temperature was raised up to 230° C. and excess ethylene glycol was distilled out, then the average molecular weight of this oligomer was about 800.

(The process for producing macrocyclic ester compound)

280 parts of the oligomer was charged into the reactor fitted with an agitator and high vacuum means and the reaction system was gradually heated. When the oligomer was melted, 1.0 parts of titanium tetrabutoxide was added in the reaction system and with simultaneous agitation, the reaction pressure was gradually reduced. At 240° C. and under 5 mmHg, distillation of both ethylene glycol and ethylene dodecanedioate initiated and the viscosity of the reaction system was gradually increased.

Up to the time the pressure reached 0.7 mmHg, 23 parts of ethylene dodecanedioate had been distilled out. At this stage the agitation became difficult, so the other parts of the oligomer were melted and added to the reactor from its bottom, then the pressure was retained at 0.3 to 0.7 mmHg and the temperature was kept at 280° C.. Further, this addition was continued so that the content weight may be kept constant.

The viscosity of the reaction system was lowered immediately after the oligomer addition, compared with that prior to the addition. The time required for the oligomer addition was 14 hours.

After the finish of this addition, the pressure was returned to the amibient pressure and the reaction was immediately terminated and 2,260 parts of ethylene dodecanedioate was obtained.

The temperature was lowered to 220° C. and 200 parts of ethylene glycol and 2 parts of sodium carbonate were added. Heating was continued at less than refluxing temperature for 3 hours and the residual ester compound in the reactor was decomposed and dissolved. Then a small amount of insoluble residue was filtered off and thereby, ethylene glycol solution containing 284 parts of bis-hydroxyethyl ester of dodecanedioic acid was obtained.

The yield of ethylene dodecanedioate which was calculated by taking into account the acid component of the bis-ester, was 97.0% relative to the dodecanedioic acid used Example 4

1.0 parts of titanium tetrabutoxide was added into the ethylene glycol solution containing 284 parts of bis-hydroxyethyl ester of dodecanedioic acid in Example 3. Then, the same reaction procedure mentioned in the process for producing macrocyclic ester compound in Example 1 was repeated and thereby, 220 parts of ethylene dodecanedioate were obtained and its yield was 95.4 % relative to the used acid component.

Comparison Example 2

The colored, crosslinked residue remaining in the reactor after the reaaction in Comparison Example 1 was slightly cooled and 100 parts of ethylene glycol and 1.0 part of sodium carbonate were added to the reactor at 210° C. Thereby, the residue gradually decomposed and after 4 hours, the ethylene glycol solution containing a large amount of insoluble material was obtained. The insoluble material was filtered off and the ethylene glycol solution containing 136 parts of bis-hydroxyethyl ester of brassylic acid was obtained.

To this ethylene glycol solution, 0.2 parts of dibutyl tinoxide were added and the same reaction as was described in the Comparison Example 1 was carried out and thereby, 7.6 parts of ethylene braasylate were obtained. Its yield was 6.9% relative to the used brassylic acid.

Example 5

(The process for producing oligomer)
1,010 parts of sebasic acid and 620 parts of ethylene glycol were used and the same process for producing oligomer in Example 3 was carried out and the oligomer was obtained. The average molecular weight of the oligomer was about 500.

(The process for producing macrocyclic ester compound)
230 parts of the oligomer was charged into a reactor fitted with an agitator and high vacuum means, the reaction system was gradually heated, and 0.5 parts of titanium tetrabutoxide was added. By agitation, the pressure was gradually reduced and at 240° C. and under 4 mmHg, distillation of both ethylene glycol and ethylene sebacate initiated. At the same time when the viscosity began to increase, the rest of the oligomer mentioned above was melted and added continuously to the reactor from its bottom for 5 hours under the reduced pressure so that a constant amount was kept. During the period of the reaction, the pressure was kept at 0.3 to 0.7 mmHg and the temperature was maintained at 280° C.. After the addition had finished, the same temperature and the same pressure were maintained for two more hours and some amount of ethylene sebacate was distilled, but the viscosity was so raised that its agitation became impossible. So, the pressure was returned to the ambient pressure and the reaction was stopped.

910 parts of ethylene sebacate were obtained and its yield to the used sebacic acid was 97.3% according to the similar calculation as mentioned in Example 3.

The residue remained in the reactor was able to be used repeatedly as described hereinbefore.

Example 6

(The process for producing oligomer)
1,150 parts of dodecanedioic acid, 760 parts of propylene glycol and 1.5 parts of titanium tetrabutoxide were charged into a reactor fitted with a distilling tower and an agitator. Those reactants were heated in the range of 150 to 200° C. and about 36 parts of water were distilled out. Afterwards, an excess of propylene glycol was distilled out at 210 to 220° C. and thus the oligomer was produced. The average molecular weight of the oligomer was about 550.

(The process for producing macrocyclic ester compound)
280 parts of the oligomer was charged into a reactor fitted with an agitator and high vacuum means. The reactant was gradually heated and the pressure was gradually reduced with agitation. At 240° C. and under 3 mmHg, distillation of both propylene glycol and propylene dodecanedioate was initiated.

In a meantime, the distillation was still continuously carried out. As the viscosity increased gradually, the temperature raised to 260° C. and the pressure decreased to the range of 0.3 to 0.5 mmHg, then all of the rest of the oligomer produced was melted and added continuously to the reactor for 25 hours so that the content amount was kept constant and thereby, the propylene dodecanedioate was continuously produced.

After the addition was finished, the reaction was further continued for one more hour. The agitation became impossible. So, the pressure was returned to the ambient and the reaction was terminated.

1,094 parts of propylene dodecanedioate were obtained. The yield was 98.8% relative to the dodecanedioic acid used with the same measurement in Example 3, which took into account the dodecandioic acid remaining in the reactor.

Comparison Example 3

Into a reactor fitted with a distilling tower and an agitator, 109 parts of dimethyl brassylate, 50 parts of ethylene glycol, 0.3 parts of titanium tetrabutoxide and 3.6 parts of methyl stearate were charged. Those reactants were heated under the ambient pressure.

At 175° C., the distillation of methanol began and, after 5 hours, 25.5 parts of methanol were distilled. The temperature raised finally to 205° C.. While the reaction pressure was gradually reduced to 40 mmHg, 23.5 parts of ethylene glycol were distilled and the ester exchange reaction was terminated at 245° C. The weight of polyethylene brassylate was 113.1 parts and its hydroxy value was 17.4.

Then, the pressure was gradually reduced further, then the distillation of ethylene brassylate containing ethylene glycol in a low concentration began at 245° C. under 5 mmHg. Since then, the temperature was kept in the range of 270 to 280° C. and the pressure was kept under 0.3 to 2 mmHg.

According as the reaction proceeded, the melt viscosity of the polymer increased gradually and, after 4 hours, the agitation became impossible. During this period, 31.1 parts of ethylene brassylate were distilled totally. After the agitation was stopped, the reaction was continued for further 4 hours, but only 2.9 parts of ethylene brassylate were distilled. Then, the reaction was terminated.

Total amount of ethylene brassylate was 34.0 parts and, as a result, the yield was no more than 31.5% relative to brassylic acid component used.

Even if a monocarboxylate was added to the reaction system as is mentioned in the process of U.S. Pat. No. 4,165,321, the prevention of the excess viscosity increase was not enough unless a specific apparatus was equipped.

Comparison Example 4

Into a reactor fitted with a distilling tower and an agitator. 109 parts of dimethyl brassylate, 50 parts of ethylene glycol and 0.3 parts of titanium tetrabutoxide were charged. Those reactant were heated under the ambient pressure.

At 170° C., the distillation of methanol began and, after 4.5 hours, 25.3 parts of methanol were distilled. The temperature raised finally to 205° C. While the reaction pressure was gradually reduced to 40 mmHg, 23.7 parts of ethylene glycol were distilled and the ester exchange reaction was terminated at 245° C.. The weight of polyethylene brassylate was 110.0 parts and its hydroxy value was 16.8.

The molten polyethylene brassylate was added dropwise at the rate of 10 parts per hour to an empty reactor, for depolymerization and cyclization, heated at 285 to 290° C. and kept under a vacuum of 0.3 to 2 mmHg in advance. During the initial 6 hours, ethylene brassylate was distilled out smoothly and the average yield for this 6 hours was 78.0% relative to the brassylate component added dropwise. But, during the rest 5 hours, the generation of ethylene brassylate was gradually decreased, and the polyethylene brassylate remained in the reactor became viscous more and more. Finally, the cyclic ester generated scarcely, and the polyester only foamed. After all, the total amount of ethylene brassylate distilled out was 56.6 parts and its yield was 52.3% relative to the brassylate used.

The dropwise addition of polyethylene brassylate to an empty reactor as is mentioned in the process of U.S. Pat. No. 4,251,448, could make the reaction proceed smoothly for the limited period, but the reaction could hardly proceed after the period, and the viscosity increased extremely.

Comparison Example 5

Into a reactor fitted with a distilling tower and an agitator, 96 parts of dimethyl brassylate, 44 parts of ethylene glycol and 0.3 parts of titanium tetrabutoxide were charged. Those reactants were heated under the ambient pressure.

After methanol was distilled for 4 hours at 170 to 205° C., the reaction pressure was reduced gradually to 40 mmHg and the temperature was raised finally to 240° C. Then, free ethylene glycol was distilled. The amount of polyethylene brassylate was 100 parts.

This polyethylene brassylate and 16 parts of stearyl alcohol were added to a reactor fitted with high vacuum means and an agitator. Since the reaction temperature was kept in the range of 270 to 280° C. and the pressure was kept under 0.3 to 2 mmHg, ethylene brassylate was distilled out gradually. But, at about the time when the reaction was continued for 8 hours, the distillation of ethylene brassylate almost stopped. The total amount of ethylene brassylate was 38.4 parts.

According to the gas chromatographic analysis of this ethylene brassylate, 8% (3 parts) of stearate alcohol had contaminated. The yield was 35.0% relative to the brassylate component used. And further, the odor of this brassylate was degraded.

The method as is mentioned in the process of Japanese unexamined application No. 120581/1980 could prevent the excess increase of the viscosity, but the yield was very low, compared with the present process, and the odor was degraded.

After the above reaction, the oligomer made by the method shown in Example 1 was added to the reaction system, and the reaction was continued further, then ethylene brassylate began to generate again. But the odor was not so excellent.

What we claim is:

1. A process for producing a macrocyclic ester compound having the general formula:

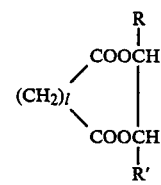

in which R and R' both denote a hydrogen atom or one denotes a hydrogen atom and the other denotes an alkyl group selected from the group consisting of methyl and ethyl, l is a positive integer in the range of 6 to 14, said process comprising:

(1) maintaining a linear ester compound having the general repeating unit formula,

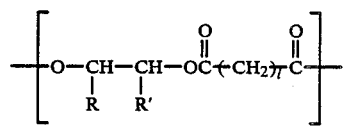

in which R, R' and l are as hereinbefore described, in a molten state with agitation under reduced pressure of 50 mmHg or less whereby the same glycol as one component of said linear ester compound is distilled off;

(2) distilling off said glycol component until said distillation terminates under reduced pressure of 40 to 50 mmHg;

(3) gradually reducing the reaction pressure of 0.1 to 1.0 mmHg to promote depolymerization-cyclization of said linear ester compound in the presence of a catalyst;

(4) distilling off said macrocyclic ester compound and said glycol to a point where agitation becomes difficult;

(5) adding the same said linear ester compound having the general repeating unit formula set forth in step (1) in which the average degree of condensation of said linear ester compound is 20 or less, said compound being added in proportion to the distillation rate of step (4); and then (6) further removing by distillation said macrocyclic ester compound and said glycol.

* * * * *